(12) United States Patent
Yatsuo et al.

(10) Patent No.: US 12,178,563 B2
(45) Date of Patent: Dec. 31, 2024

(54) MAGNETIC RESONANCE IMAGING APPARATUS, METHOD FOR CONTROLLING THE SAME, AND CONTROL PROGRAM OF MAGNETIC RESONANCE IMAGING APPARATUS

(71) Applicant: FUJIFILM Healthcare Corporation, Kashiwa (JP)

(72) Inventors: Takeshi Yatsuo, Chiba (JP); Kazuyuki Kato, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 164 days.

(21) Appl. No.: 17/901,935

(22) Filed: Sep. 2, 2022

(65) Prior Publication Data
US 2023/0078113 A1   Mar. 16, 2023

(30) Foreign Application Priority Data
Sep. 15, 2021 (JP) ................. 2021-150455

(51) Int. Cl.
*A61B 5/055* (2006.01)
*A61B 5/00* (2006.01)
*G01R 33/563* (2006.01)

(52) U.S. Cl.
CPC ............ *A61B 5/055* (2013.01); *A61B 5/7207* (2013.01); *A61B 5/7285* (2013.01); *G01R 33/56375* (2013.01)

(58) Field of Classification Search
CPC ..... A61B 5/055; A61B 5/7207; A61B 5/7285; G01R 33/56375; G01R 33/5673; G01R 33/56509
See application file for complete search history.

(56) References Cited

U.S. PATENT DOCUMENTS

2005/0054910 A1\* 3/2005 Tremblay ............... A61B 34/20
                                                   600/414
2011/0311119 A1\* 12/2011 Jeanne ................. A61B 5/0255
                                                   382/128
(Continued)

FOREIGN PATENT DOCUMENTS

| JP | 9-28689 A | 2/1997 |
| JP | 2006-346235 A | 12/2006 |
| JP | 2009-183510 A | 8/2009 |

OTHER PUBLICATIONS

Japanese official action dated Dec. 12, 2023 (and English translation thereof) in connection with Japanese Patent Application No. 2021-150455.

*Primary Examiner* — Bo Joseph Peng
(74) *Attorney, Agent, or Firm* — Paul Teng

(57) ABSTRACT

An object of the invention is to perform MRI imaging which is less likely to be affected by a body motion without prolonging an imaging time. The control unit takes in images captured by the camera at a predetermined frame rate. The imaging pulse sequence is divided into small sequences at a time width corresponding to the frame rate of the camera. The control unit, before causing the imaging unit to execute one small sequence, detects a displacement of the subject with respect to a predetermined reference position or a motion speed of the subject based on an image of the latest frame, and causes the imaging unit to execute the small sequence when a detection result is within a predetermined allowable range and waits until an image of a next frame is taken in according to the frame rate without causing the imaging unit to execute the small sequence when the detection result exceeds the allowable range.

14 Claims, 8 Drawing Sheets

(56) References Cited

U.S. PATENT DOCUMENTS

| | | |
|---|---|---|
| 2015/0208981 A1 | 7/2015 | Oh et al. |
| 2016/0073993 A1* | 3/2016 | Ouyang ............... A61B 5/0035 |
| | | 600/411 |
| 2020/0110145 A1* | 4/2020 | Zeller .................. A61B 5/7207 |
| 2021/0121092 A1* | 4/2021 | Kawajiri ................ A61B 5/055 |

* cited by examiner

FIG. 7
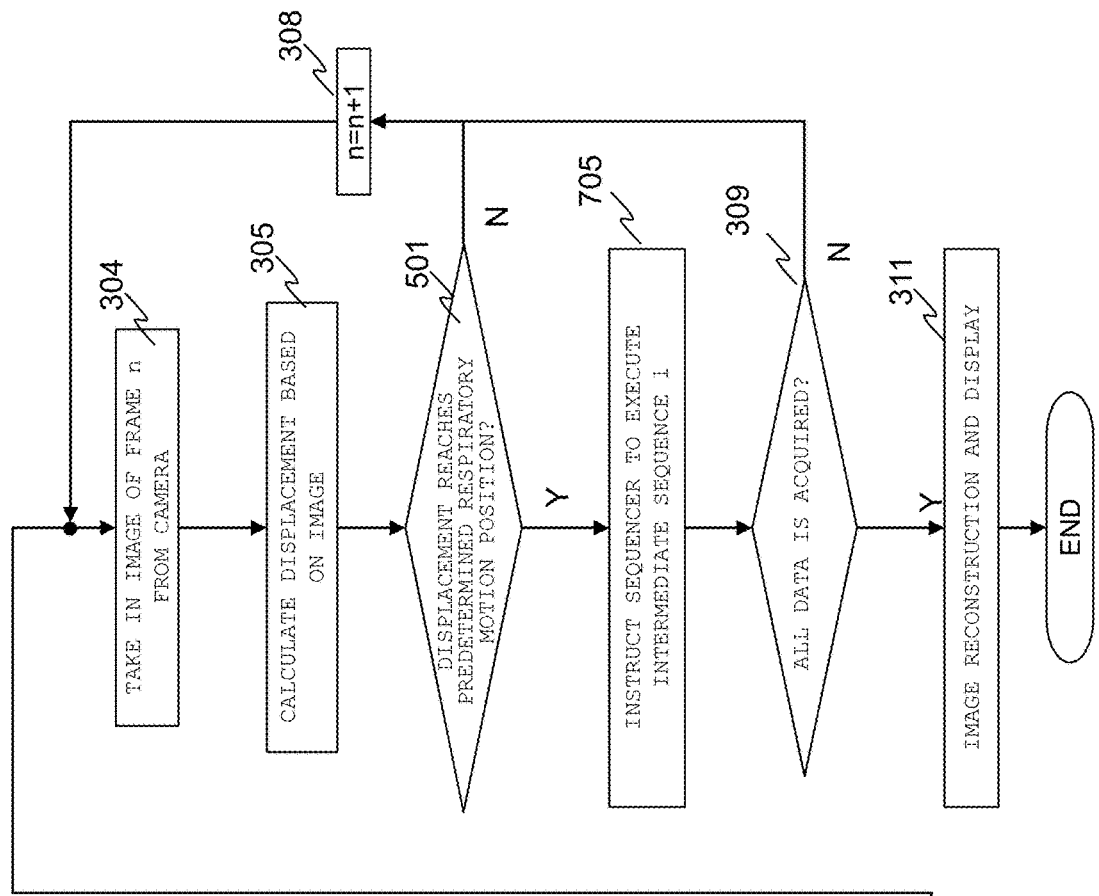
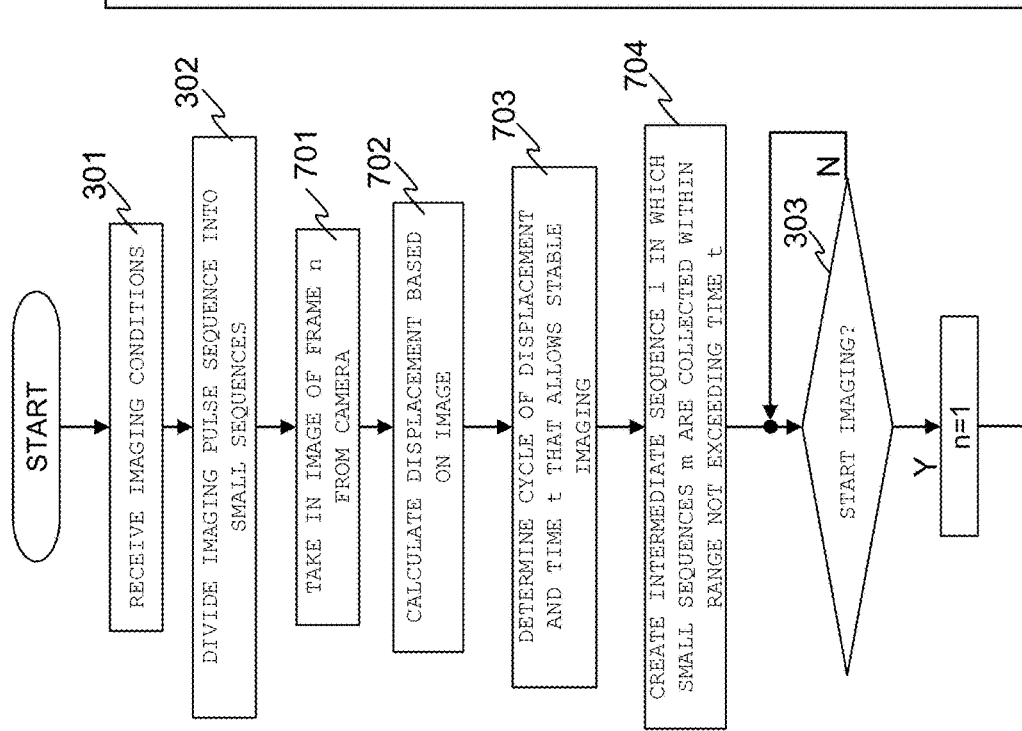

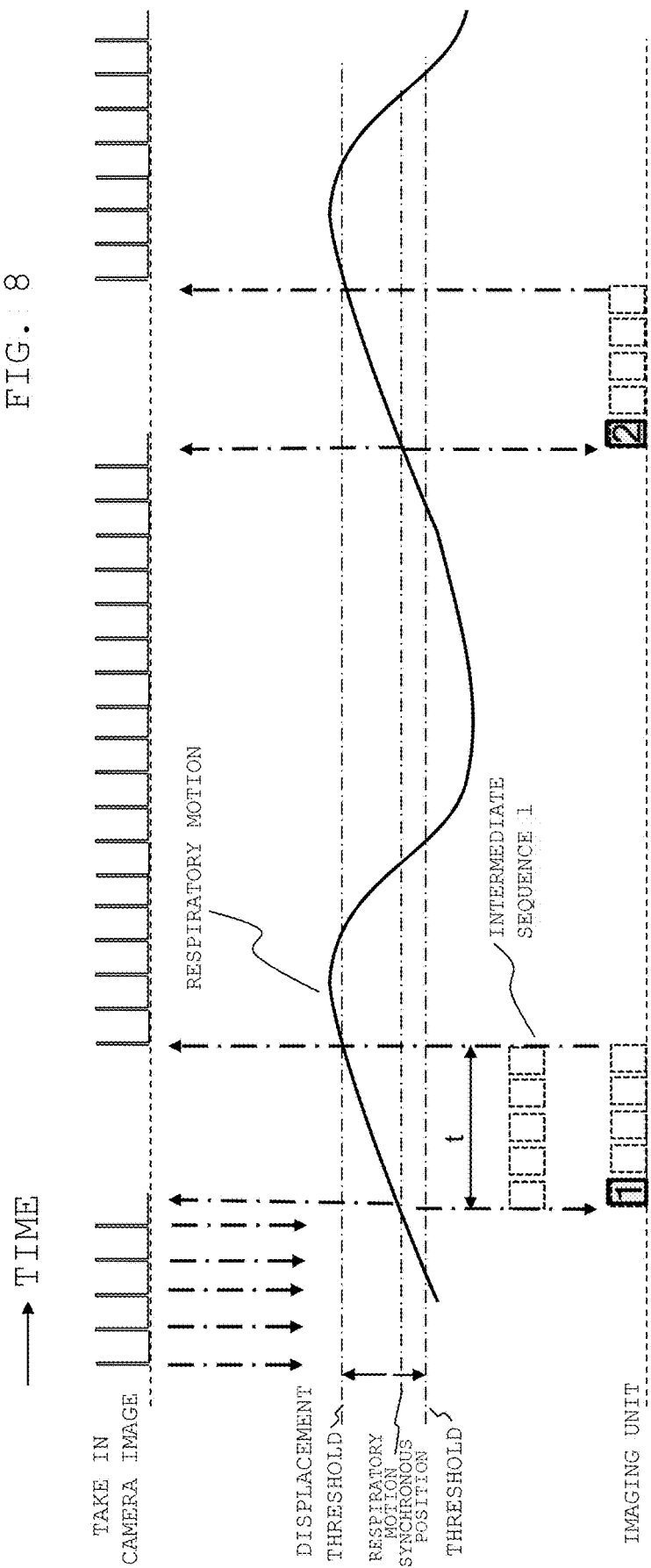

MAGNETIC RESONANCE IMAGING APPARATUS, METHOD FOR CONTROLLING THE SAME, AND CONTROL PROGRAM OF MAGNETIC RESONANCE IMAGING APPARATUS

BACKGROUND OF THE INVENTION

1. Field of the Invention

The present invention relates to a device having a function of observing a motion of a subject in a magnetic resonance imaging (hereinafter, referred to as "MRI") apparatus, which measures a nuclear magnetic resonance (hereinafter, referred to as "NMR") signal from hydrogen, phosphorus, or the like in the subject and images a nuclear density distribution, a relaxation time distribution, and the like.

2. Related Art

The MRI apparatus is an apparatus that measures an NMR signal generated by nuclear spin of atoms forming tissue of a subject, particularly a human body, and two-dimensionally or three-dimensionally images morphologies or functions of a head, an abdomen, limbs, and the like of the subject. In imaging, the NMR signal is applied with different phase encoding by a gradient magnetic field to be subjected to frequency encoding, and is measured as time series data. The measured NMR signal is reconstructed into images by two-dimensional or three-dimensional Fourier transform.

Imaging using the MRI apparatus takes about tens of minutes to one hour, and when the subject moves during the imaging, an artifact occurs in the image.

For this reason, JP-A-2006-346235 discloses an invention of determining presence or absence of a body motion by acquiring still images of a subject before the start of MRI imaging and during MRI imaging by a video camera and obtaining a correlation function between the two still images. When a body motion is present, the MRI imaging is performed again from the start.

Further, in JP-A-9-28689, during MRI imaging, an image of a subject is captured by a TV camera, and when a motion of the subject is no less than an allowable range, MR data at a time point of the motion is deleted, recaptured, or corrected. Alternatively, an RF pulse and a gradient magnetic field are optimized to cancel an influence of the motion of the subject.

SUMMARY OF THE INVENTION

In the invention of JP-A-2006-346235, a body motion of the subject is detected during the MRI imaging, and the MRI imaging is performed again from the start when a body motion occurs, which requires a longer time for imaging.

In addition, in JP-A-9-28689, when a body motion occurs during imaging, the MR data acquired during such period needs to be specified in order to delete or to recapture the MR data acquired during the imaging. In the MRI imaging, an operation of acquiring one echo signal (MR data) that is acquired by applying predetermined phase encoding is repeated 256 times or 512 times while changing the phase encoding. A time required to acquire one echo signal is as fairly short as 1 ms to 2 ms. To accurately specify which echo signal is acquired at a time when the body motion occurs and to delete or recapture the echo signal, the TV camera and the MRI apparatus are required to be synchronized, which is not easy.

An object of the invention is to perform MRI imaging which is less likely to be affected by a body motion without prolonging an imaging time.

In order to solve the above problems, the invention provides an MRI apparatus as follows. That is, an MRI apparatus of the invention includes: a static magnetic field generating device configured to apply a static magnetic field to an imaging region; an imaging unit configured to apply a high-frequency magnetic field pulse and a gradient magnetic field pulse to a subject arranged in the imaging region and acquire a nuclear magnetic resonance signal generated from the subject; a control unit configured to cause the imaging unit to repeatedly execute the application of the high-frequency magnetic field pulse and the gradient magnetic field pulse and the acquisition of the nuclear magnetic resonance signal at predetermined timings in accordance with a predetermined imaging pulse sequence and cause the imaging unit to acquire a necessary number of nuclear magnetic resonance signals for image reconstruction; and a camera configured to continuously and optically image the subject arranged in the imaging region during an operation of the imaging unit.

The control unit takes in images captured by the camera at a predetermined frame rate. The imaging pulse sequence is divided into small sequences at a time width corresponding to the frame rate of the camera.

The control unit causes the imaging unit to sequentially execute the small sequences at a time interval corresponding to the frame rate by repeating an operation of: before causing the imaging unit to execute one small sequence, detecting a displacement of the subject with respect to a predetermined reference position or a motion speed of the subject based on an image of the latest frame, and causing the imaging unit to execute the small sequence when a detection result is within a predetermined allowable range and waiting until an image of a next frame is taken in according to the frame rate without executing the small sequence when the detection result exceeds the allowable range.

According to the invention, the imaging pulse sequence is divided into small sequences at a time width corresponding to the frame rate of the camera, the displacement and the motion speed of the subject are detected before execution of the small sequence, and the imaging unit waits until a next timing without executing the small sequence when the detection result exceeds the allowable range. Therefore, it is not necessary to delete or recapture NMR signal data after the imaging, and the MRI imaging in which an influence of the body motion of the subject is reduced can be performed without prolonging the imaging time.

BRIEF DESCRIPTION OF THE DRAWINGS

FIG. 7 is a flowchart showing operations of the central processing unit 110 of an MRI apparatus according to a third embodiment.

FIG. 8 is a time chart showing a displacement and a motion of the subject, timings for the central processing unit 110 of the MRI apparatus to take in camera images, and imaging periods of the imaging unit 300 according to the third embodiment.

DESCRIPTION OF EMBODIMENTS

Embodiments of the invention will be described with reference to the drawings.

First Embodiment

An MRI apparatus according to a first embodiment will be described with reference to FIGS. 1 to 4. The MRI apparatus according to the present embodiment includes a camera that continuously and optically images a subject arranged in an imaging region. The control unit takes in images captured by the camera at a predetermined frame rate. The imaging pulse sequence is divided into small sequences at a time width corresponding to the frame rate. The control unit repeats an operation of: before causing the imaging unit to execute one small sequence, detecting a displacement of the subject with respect to a predetermined reference position or a motion speed of the subject based on an image of the latest frame, and causing the imaging unit to execute the small sequence when a detection result is within a predetermined allowable range and waiting until an image of a next frame is taken in without causing the imaging unit to execute the small sequence when the detection result exceeds the allowable range.

That is, the control unit is configured to determine whether a positional deviation or a body motion in the subject that exceeds the allowable range occurs at a timing synchronized with the frame rate at which an image is taken in, and determine whether to execute the small sequence during a period until the image of the next frame is taken in.

Accordingly, when the positional deviation or the body motion of the subject exceeds the allowable range, the small sequence is not executed during a period immediately thereafter, and the control unit waits until the image of the next frame is taken in. Therefore, NMR signal data is not acquired during a period in which the positional deviation or the body motion occurs in the subject. Therefore, it is not necessary to delete or recapture the NMR signal data after imaging, and MRI imaging in which an influence of the body motion of the subject is reduced can be performed without prolonging an imaging time.

Configuration of MRI Apparatus

Figure 1:
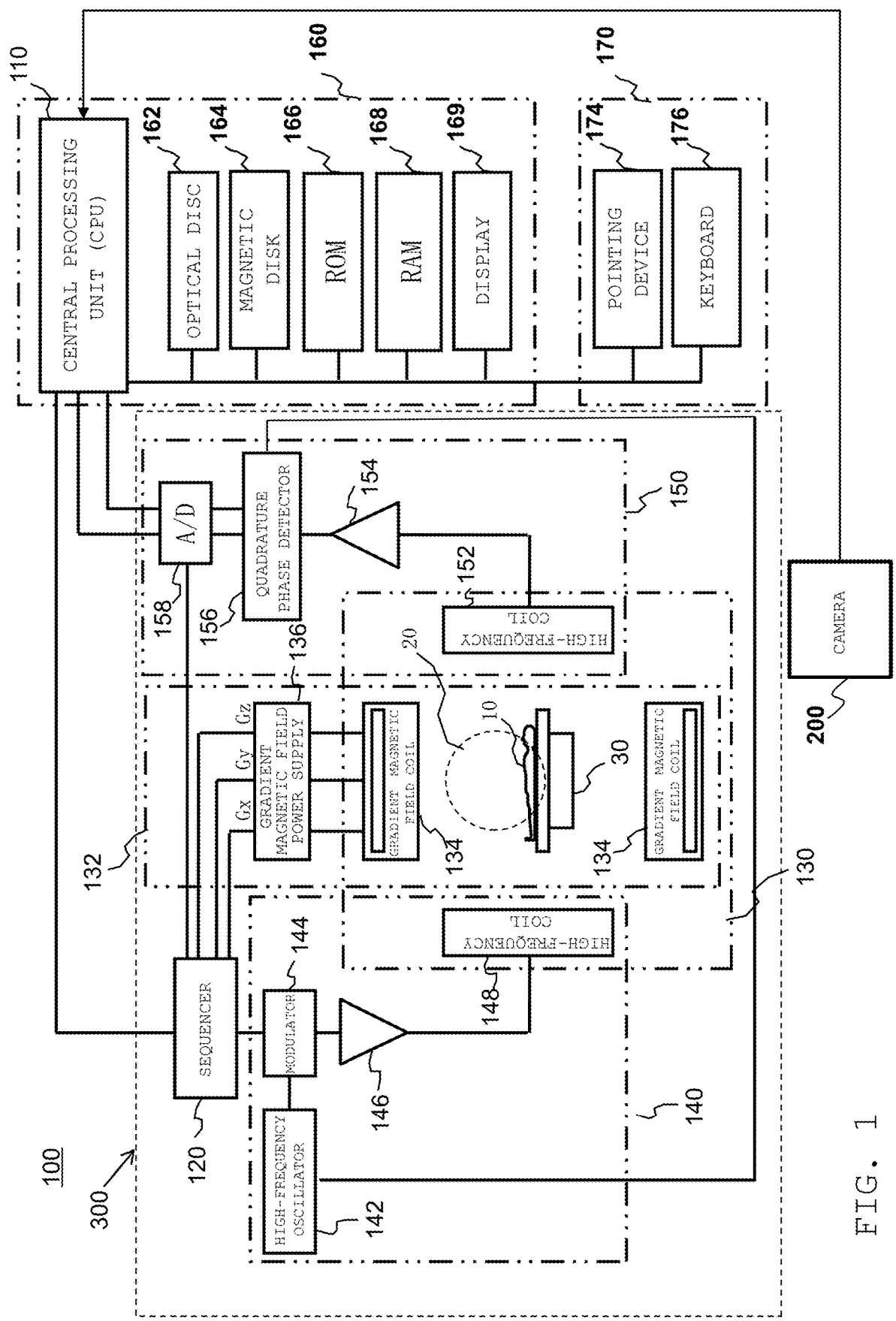
FIG. 1 is a block diagram showing an overall configuration of an MRI apparatus according to a first embodiment of the invention.

Next, a configuration of an MRI apparatus 100 according to the present embodiment will be described with reference to FIG. 1.

The MRI apparatus 100 includes a static magnetic field generating device 130, a gradient magnetic field generating device 132 that applies a gradient magnetic field pulse to a subject 10, an RF signal irradiation device 140 that irradiates the subject 10 with a high-frequency magnetic field pulse (hereinafter denoted as RF pulse), a receiving device 150 that receives an echo signal which is an NMR signal from the subject 10, a processing device 160 including a central processing unit (hereinafter denoted as CPU) 110, a sequencer 120, an operating device 170 for performing various operations related to data input, imaging, and the like, a bed 30, and a camera 200.

The static magnetic field generating device 130 applies a fairly uniform magnetic field to an imaging region 20.

The bed has the subject 10 placed thereon, and at least a part of the subject 10 to be imaged is arranged in the imaging region 20.

The gradient magnetic field generating device 132, the RF signal irradiation device 140, and the receiving device 150 form an imaging unit 300. The imaging unit 300 applies the RF pulse and the gradient magnetic field pulse to the subject 10 arranged in the imaging region 20, and acquires the NMR signal generated from the subject.

The central processing unit 110 functions as the control unit, and controls the sequencer 120 to cause the imaging unit 300 to repeatedly execute the application of the high-frequency magnetic field pulse and the gradient magnetic field pulse and the acquisition of the nuclear magnetic resonance signal at predetermined timings in accordance with a predetermined imaging pulse sequence. The central processing unit 110 also functions as an image reconstruction unit to process a necessary number of NMR signals acquired by the imaging unit 300 for image reconstruction and generate a tomographic image of the subject 10.

During operations of the imaging unit 300, the camera 200 continuously and optically images the subject 10 arranged in the imaging region 20. The central processing unit 110 sequentially takes in images captured by the camera at a predetermined frame rate.

Further, each part will be described in detail. A description of a specific configuration of the static magnetic field generating device 130 is omitted. The static magnetic field generating device 130 generates a fairly uniform static magnetic field in a direction orthogonal to a body axis of the subject 10 in a space around the subject 10 in a case of a vertical magnetic field method, and in the body axis direction in a case of a horizontal magnetic field method. The static magnetic field generating device 130 is provided around the subject 10 in order to generate the static magnetic field described above, and includes a permanent magnet, a normal conducting magnet, or a superconducting magnet as a static magnetic field generation source.

The gradient magnetic field generating device 132 includes gradient magnetic field coils 134 wound in three axial directions including an X axis, a Y axis, and a Z axis, which form a coordinate system of the MRI apparatus 100, for example, a static coordinate system, and a gradient magnetic field power supply 136 that supplies a drive current for generating a gradient magnetic field to each of the gradient magnetic field coils. The gradient magnetic field power supply 136 operates in accordance with an instruction from the sequencer 120, and supplies the drive currents to the gradient magnetic field coils 134 in the three axial directions including the X axis, the Y axis, and the Z axis. Accordingly, the gradient magnetic field coil 134 generates a gradient magnetic field Gx, Gy, Gz in the three axial directions including the X axis, the Y axis, and the Z axis. The generated gradient magnetic field Gx, Gy, Gz is applied to the subject 10 in the imaging region 20. For example, when imaging, a slice direction gradient magnetic field pulse (Gs) is applied in a direction orthogonal to a slice plane as an imaging cross section in accordance with the imaging pulse sequence, thereby setting the slice plane with respect to the subject 10. A phase encoding direction gradient magnetic field pulse (Gp) and a frequency encoding direction gradient magnetic field pulse (Gf) are applied in the other two directions which are orthogonal to the slice plane and orthogonal to each other, thereby encoding position information in each direction in the NMR signal as an echo signal.

The RF signal irradiation device 140 irradiates the subject 10 with the RF pulse, and causes nuclear spins of atoms forming biological tissue of the subject 10 to generate nuclear magnetic resonance. For example, the RF signal irradiation device 140 includes a high-frequency oscillator 142, a modulator 144, a high-frequency amplifier 146, and a transmission-side high-frequency coil 148 that operates as a transmission coil. A high-frequency pulse output from the high-frequency oscillator 142 is subjected to amplitude modulation by the modulator 144 at a timing instructed by the sequencer 120, and the high-frequency pulse subjected to the amplitude modulation is amplified by the high-frequency amplifier 146. The amplified high-frequency pulse is supplied to the high-frequency coil 148 arranged close to the subject 10. Accordingly, the high-frequency coil 148 irradiates the subject 10 with the RF pulse. In the biological tissue of the subject 10 irradiated with the RF pulse, the nuclear spins of atoms forming the biological tissue cause the nuclear magnetic resonance, and emit the NMR signal which is an echo signal.

The receiving device 150 detects and processes the emitted NMR signal. The receiving device 150 includes a reception-side high-frequency coil 152 that operates as a receiving coil, a signal amplifier 154 that amplifies a received NMR signal, a quadrature phase detector 156, and an A/D converter 158 that converts an analog signal into a digital signal. The high-frequency coil 152 detects the NMR signal emitted from the subject, and the signal amplifier 154 amplifies the detected NMR signal. The quadrature phase detector 156 divides the NMR signal into two systems of signals orthogonal to each other at a timing instructed by the sequencer 120. The divided two systems of signals are converted into digital amounts by the A/D converter 158 respectively, and sent to the central processing unit 110.

The transmission-side high-frequency coil 148 and the gradient magnetic field coils 134 are arranged in a static magnetic field space of the static magnetic field generating device 130 in which the subject 10 is arranged. The transmission-side high-frequency coil 148 and the gradient magnetic field coils 134 face the subject 10 in the case of the vertical magnetic field method, and surround the subject 10 in the case of the horizontal magnetic field method. The reception-side high-frequency coil 152 faces or surround the subject 10.

The sequencer 120 outputs a control signal (command) to the RF signal irradiation device 140, the gradient magnetic field generating device 132, and the receiving device 150 at the predetermined timing under control of the central processing unit 110. Accordingly, the RF pulse and the gradient magnetic field pulse are applied to the subject at a timing in accordance with the predetermined imaging pulse sequence, and the imaging unit 300 is caused to repeatedly execute the acquisition of the NMR signal while changing a phase encoding amount.

The processing device 160 includes, in addition to the central processing unit 110, external storage devices such as an optical disc 162 and a magnetic disk 164 for storing information, a ROM 166 for storing necessary data and programs for processing, a RAM 168 that performs temporary storing for processing, and a display 169 such as a CRT. Accordingly, the processing device 160 performs various data processing, displays and storages processing results, and the like. For example, when a processing result received and processed by the receiving device 150 is input from the receiving device 150 to the processing device 160, processing such as signal processing and image reconstruction is performed by the central processing unit 110 of the processing device 160. The tomographic image of the subject 10, which is a result thereof, is displayed on the display 169, and is recorded on the optical disc 162, the magnetic disk 164, or the like of the external storage devices as necessary. Although not shown in the drawing, the tomographic image may also be printed or transmitted to another system.

The operating device 170 includes a pointing device 174 such as a track ball or a mouse, and a keyboard 176. An operator inputs various kinds of control information of the MRI apparatus 100 and control information on processing performed by the processing device 160 via the operating device 170. The operating device 170 is arranged close to the display 169, and the operator can interactively perform an operation through the operating device 170 while viewing the image displayed on the display 169. The operating device 170 is not limited thereto, and may include, for example, a touch panel provided on a display surface of the display 169. The operating device 170 is provided in an operation room away from a main body of the MRI apparatus 100. A part of the operating device 170 is also provided in the main body of the MRI apparatus 100 and the bed 30. Accordingly, the configuration allows the operator to perform necessary operations near the subject 10.

A nuclide to be imaged of the subject 10 of the MRI apparatus 100 is, for example, as a nuclide widely used in clinical practice, hydrogen nucleus, that is, proton, which is a main substance forming the subject. The MRI apparatus 100 images information on a spatial distribution of proton density and a spatial distribution of relaxation time of excited state. Accordingly, the MRI apparatus 100 can two-dimensionally or three-dimensionally image morphologies or functions of a head, an abdomen, limbs, and the like of the subject 10, and display a reconstructed image on the display 169. The reconstructed image is stored in the optical disc 162 or the magnetic disk 164 as necessary. The image is printed based on an operation or transmitted to another necessary system.

Configuration of Camera 200

Figure 2:
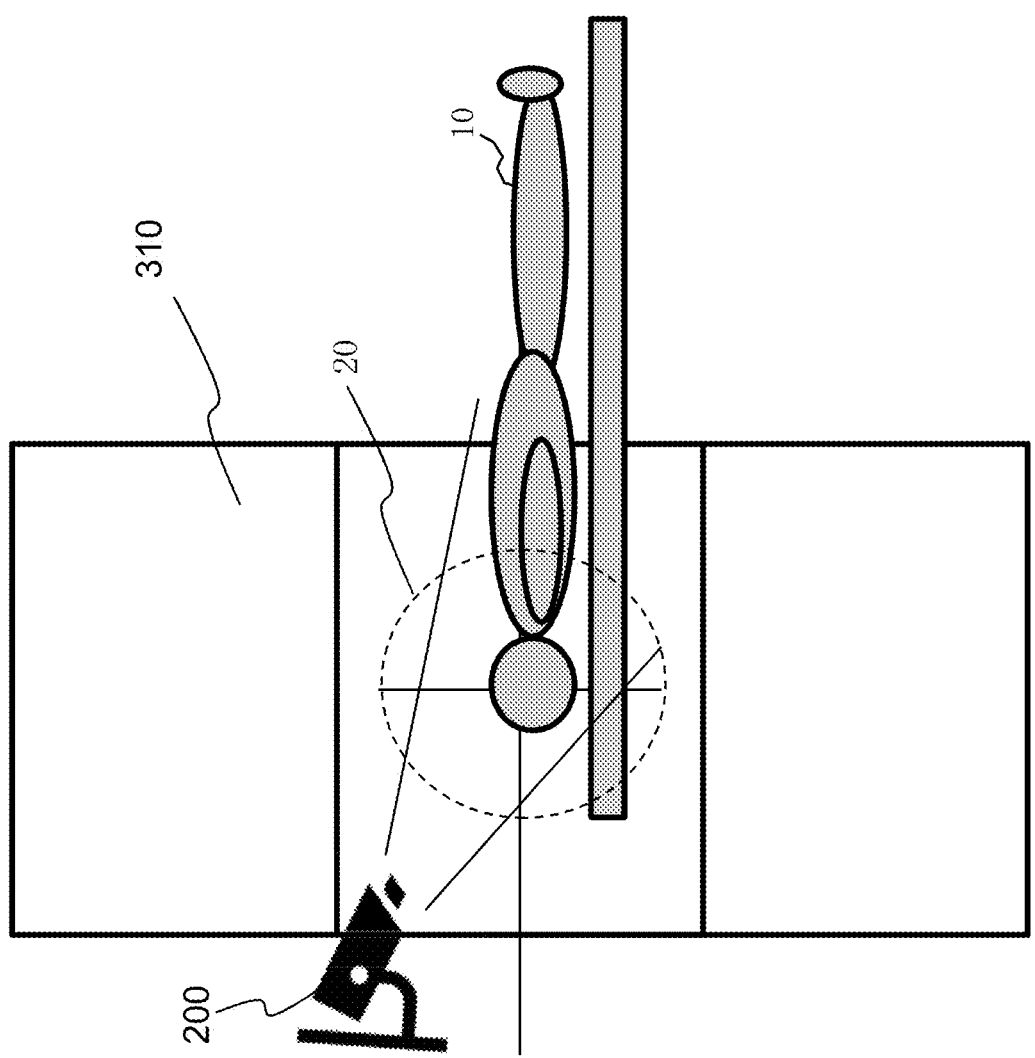
FIG. 2 is a diagram showing an example of an arrangement of a camera in the MRI apparatus according to the first embodiment.

FIG. 2 shows an arrangement of the camera 200 of the MRI apparatus 100. The camera 200 is mounted on the bed 30 and is provided at a position that allows to image the subject 10 arranged in the imaging region 20.

The camera 200 may be arranged as a part of a gantry 310 built-in with the imaging unit 300 of the MRI apparatus 100, or may be arranged to image the subject 10 from the outside of the gantry 310.

The camera 200 optically captures continuous images at a frame rate equal to or higher than the predetermined frame rate. For example, it is desirable that the camera can capture 30 or more images per second. The central processing unit 110 takes in the images from the camera 200 at the predetermined frame rate. The frame rate at which the camera 200 captures images may be synchronized with the frame rate at which the central processing unit 110 takes in the images, or may not be synchronized if the frame rate of the camera is higher than the frame rate at which the central processing unit 110 takes in the images. The operator sets the frame rate at which the central processing unit 110 takes in the images via the operating device 170. When the frame rate at which the camera 200 captures the images is to be synchronized with the frame rate at which the central processing unit 110 takes in the images, the central processing unit 110 sets the frame rate set by the operator to the camera 200.

In addition, the camera 200 includes a structure that shields electromagnetic noise so that the imaging unit 300 does not generate noise due to electromagnetic noise generated by the camera 200.

Further, the camera 200 includes a structure that shields a large magnetic field, a magnetic field having a large chronological change, or a high frequency from the outside so as to function as the camera 200 even when receiving a strong magnetic field generated by the static magnetic field generating device 130, a magnetic field having a large chronological change applied by the gradient magnetic field coils 134, or an RF pulse irradiated from the high-frequency coil 148.

The number of cameras 200 arranged in the MRI apparatus 100 is not limited to one. In order to image a position and a motion of the subject 10 with respect to each arrangement thereof, it is more desirable to arrange two cameras 200 in front of and at the rear of the subject 10.

In addition, the gantry 310 of the MRI apparatus has a cylindrical shape or a parallel plate shape, and thus it is difficult for light to enter the imaging region 20. Therefore, in order to increase an SN ratio of the image of the optical camera 200, it is desirable to arrange an illuminating device that irradiates the imaging region 20 with light.

Digital images captured by the camera 200 are taken in by the central processing unit 110 at the predetermined frame rate. By controlling the imaging unit 300 as described below using the images captured by the camera 200, the central processing unit 110 causes the imaging unit 300 to execute the imaging pulse sequence for implementing an imaging method selected by the operator. In accordance with the imaging pulse sequence, the imaging unit 300 acquires 256 or 512 echo signals, which is necessary for image reconstruction, while changing the phase encoding amount.

The imaging pulse sequence is stored in advance for each of a plurality of imaging methods in a memory built in the central processing unit 110, the magnetic disk 164, the ROM 166, or the like. The operator selects an imaging method via the operating device 170, and further inputs imaging conditions (repetition time TR and the like). Accordingly, the central processing unit 110 generates the imaging pulse sequence corresponding to the set imaging conditions.

Figure 3:
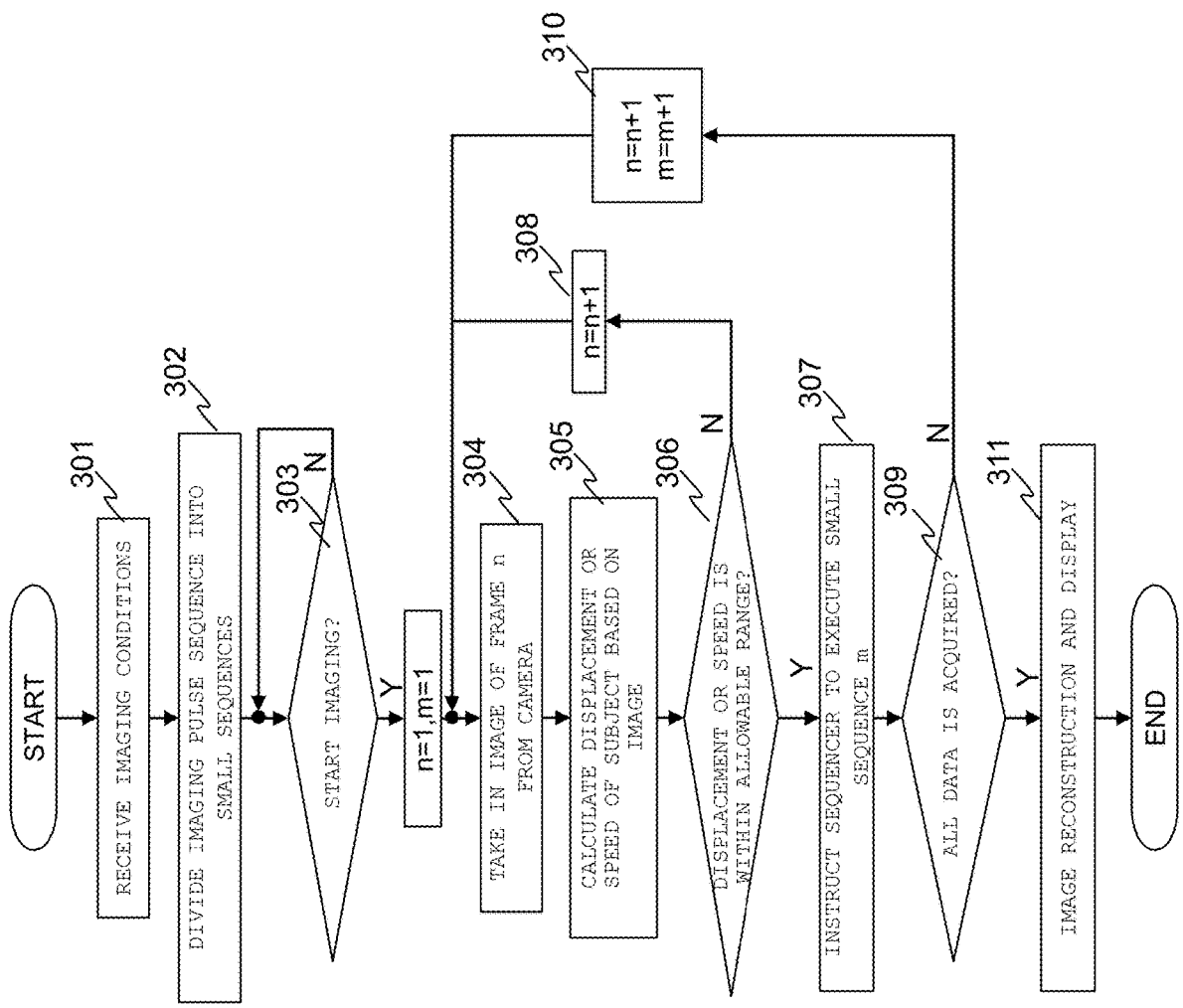
FIG. 3 is a flowchart showing operations of a central processing unit 110 of the MRI apparatus according to the first embodiment.
Figure 4:
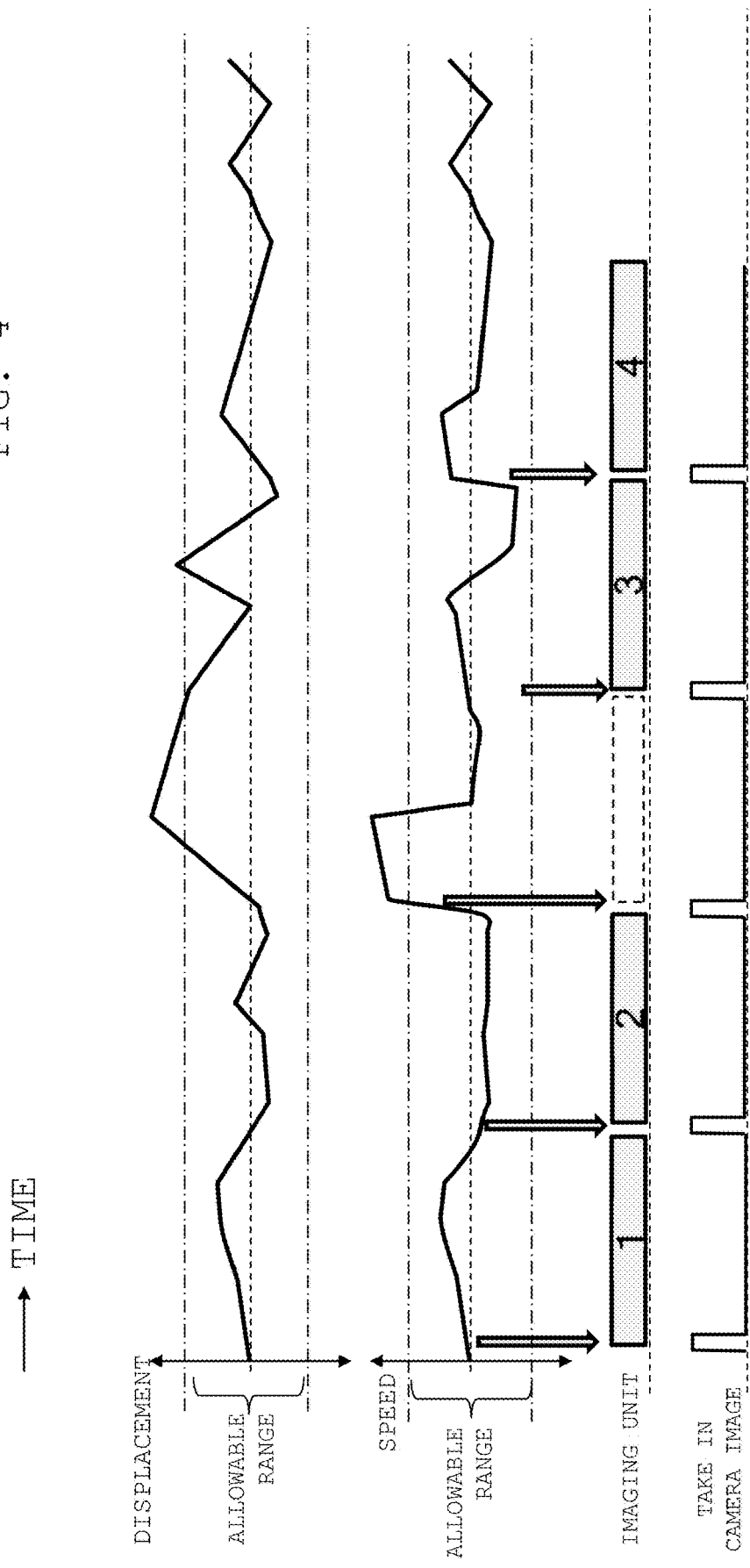
FIG. 4 is a time chart showing a displacement and a motion of a subject, timings for the central processing unit 110 of the MRI apparatus to take in camera images, and imaging periods of an imaging unit 300 according to the first embodiment.

Here, the central processing unit 110 is a processor (computer) such as a central processing unit (CPU) or a graphics processing unit (GPU), and reads and executes a program stored in the ROM 166 in advance so as to implement processing as shown by a flowchart of FIG. 3 by software. A part or all of the processing in FIG. 3 may also be implemented by hardware. For example, a part or all of the central processing unit 110 may be configured using a custom IC such as an application specific integrated circuit (ASIC) or a programmable IC such as a field-programmable gate array (FPGA), and the programmable IC may be subjected to circuit design to perform the processing in FIG. 3.

The flowchart of FIG. 3 will be described in detail below.

It is assumed that the subject 10 is placed on the bed 30 and is arranged in the imaging region 20 in advance.

Step 301

The central processing unit 110 receives the frame rate at which images are taken in from the camera 200 and the imaging conditions (imaging method, repetition time TR, TE, and the like) of the imaging pulse sequence from the operator via the operating device 170. The frame rate set here for taking in the images may be any value as long as within a maximum frame rate at which the camera 200 can capture images. Here, an example will be described in which the central processing unit 110 takes in the images from the camera 200 at a frame rate of 33 images per second, that is, at a time interval of 30 ms. The frame rate at which images are taken in from the camera 200 may be a predetermined value instead of being received from the operator.

Step 302

The central processing unit 110 adjusts a reference imaging pulse sequence for each imaging method that is stored in advance in the ROM 166 or the like using the imaging conditions received from the operator in step 301, and generates an imaging pulse sequence for acquiring 256 or 512 NMR signals (echo signals), which is necessary for image reconstruction, under the imaging conditions.

The central processing unit 110 divides the generated imaging pulse sequence into small sequences at a time width corresponding to the frame rate set in step 301. Here, the set frame rate is 33 images per second, and thus the central processing unit 110 divides the imaging pulse sequence into periods of 30 ms. In general, since the time (TR) required to acquire one NMR signal is 1 ms to 2 ms, one small sequence (30 ms) is a sequence in which 15 to 30 echo signals are acquired.

Step 303

When the operator instructs to start imaging via the operating device 170, the central processing unit 110 proceeds to step 304.

Step 304

The central processing unit 110 instructs the camera 200 to start imaging of the subject 10, and takes in an image of a frame n (n=1) at the frame rate set in step 301.

Step 305

The central processing unit 110 detects a position of the subject based on the image of the frame n (n=1) taken in during step 304.

Alternatively, a difference between the image of the frame n and an image of a previous frame (n−1) is calculated to calculate a speed (displacement vector). Thus, a motion of the subject 10 can be calculated.

The central processing unit 110 may select an image of a reference frame (n=0), and calculate a difference between the image of the reference frame (n=0) and the image of the frame n taken in during step 304 as the displacement with respect to the reference position.

Alternatively, the speed (displacement vector) may be integrated from the start of imaging to the current point to obtain the displacement.

The reference frame (n=0) may be an image at any timing, for example, an image of a frame at a predetermined timing before step 304 or the image of the frame n (n=1) acquired in an initial step 304. Specifically, the frame at the predetermined timing before step 304 may be a frame at a time point when the subject 10 is arranged in the imaging region 20, or a frame at a time point when a door of an imaging room is closed after the subject 10 is arranged in the imaging region 20. Alternatively, the frame may also be a frame at a time point when the operating device 170 instructs to start imaging.

In order to improve detection accuracy of the position or the displacement with respect to the reference position or the motion (speed), a marker may be attached to the subject 10 or the high-frequency coil (receiving coil) 152. For example, a rectangular non-magnetic object arranged in a lattice shape can be attached to clothing of the subject 10, the receiving coil, or the like as the marker. The non-magnetic object preferably has upright corner edges.

Steps 306, 307, and 308

The central processing unit 110 determines whether the position (displacement) or the motion (speed) calculated in step 305 is within each predetermined allowable range.

When the position (displacement) or the motion (speed) is within the allowable range, the central processing unit 110 determines that imaging is possible, proceeds to step 307, and delivers a first small sequence m (m=1) of the imaging pulse sequence to the sequencer 120 and instructs that the small sequence is executed. Accordingly, the sequencer 120 causes each unit of the imaging unit 300 to execute the small sequence m (m=1), and acquires an echo signal m (m=1). The delivery of the small sequence to the sequencer 120 may not be performed one by one, and some small sequences may be delivered collectively.

On the other hand, in step 306, when the position (displacement) or the motion (speed) exceeds the allowable range, the central processing unit 110 determines that imaging is not possible, returns to step 304 without causing the imaging unit 300 to execute the small sequence, and waits until an image of a next frame (n+1) is taken in from the camera 200 in accordance with the frame rate.

The central processing unit 110 repeats steps 304 to 306 for the image obtained in the frame (n+1). Specifically, the central processing unit 110 detects the position of the subject 10 with respect to the image of the frame (n+1), or calculates the motion (speed) by obtaining a difference from the frame n, or calculates the displacement by obtaining a difference from the image of the reference frame (n=0). When the calculated position (displacement) or motion (speed) is within the allowable range, the central processing unit 110 causes the sequencer 120 to execute the small sequence m (step 308).

Steps 309 and 310

After the echo signal m (m=1) is acquired in step 307, the central processing unit 110 proceeds to step 309 to determine whether a predetermined number of echo signals m necessary for image reconstruction (m=256 or 512) are all acquired. When not all the echo signals m are acquired, the central processing unit 110 returns to step 304 and repeats steps 304 to 307.

In this manner, the MRI apparatus according to the present embodiment can acquire the images from the camera 200 at the predetermined frame rate, and repeat the operation of: obtaining the position (displacement) or the motion (speed) of the subject 10 based on the image, and executing the small sequence m to acquire the echo signal m when the position (displacement) or the motion (speed) is within the allowable range and waiting until the next image is acquired without executing the small sequence m when the position (displacement) or the motion (speed) exceeds the allowable range. Accordingly, all the echo signals m (m=1 to 256 or 512) can be acquired by sequentially executing the small sequences m (m=1 to 256 or 512).

Step 311

The central processing unit 110 reconstructs the tomographic image or the like of the subject 10 by performing predetermined image reconstruction using all the obtained echo signals m (m=1 to 256 or 512), and displays the reconstructed tomographic image or the like on the display 169. The reconstructed image is stored in the magnetic disk 164 or the like as necessary.

As described above, in the present embodiment, only when the position (displacement) or the motion (speed) of the subject 10 is within the allowable range, the small sequence is executed immediately thereafter to acquire the echo signal, and thus the acquired echo signal is less likely to be affected by the motion or the displacement of the subject 10. Therefore, it is possible to generate the tomographic image of the subject 10 in a state in which no sudden motion of the person occurs, that is, in a state in which the subject is stable.

Therefore, even if a body motion of the subject occurs during the MRI imaging, it is not necessary to perform the MRI imaging again from the start, or to delete or recapture the echo signal acquired during a period of the body motion, and the imaging can be completed without prolonging the imaging time. Accordingly, the MRI apparatus according to the present embodiment can perform MRI imaging which is less likely to be affected by a body motion without prolonging the imaging time.

Second Embodiment

An MRI apparatus according to a second embodiment will be described.

Motions of the subject 10 are classified into three types: a) a random motion present constantly and captured as a background noise, b) a cyclic motion synchronized with human respiratory motion or heartbeat, and c) a sudden human motion.

In the first embodiment, the small pulse sequence is executed to avoid the sudden human motion in c), but in the second embodiment, imaging control is executed using the cyclic motion in b). For example, a small pulse sequence is executed in synchronization with a displacement caused by a respiratory motion of the subject 10 to acquire NMR data. Accordingly, it is possible to achieve the same effect as in the related art in which a respiratory motion sensor is mounted on the subject 10 to perform respiratory synchronous imaging, but without using a respiratory motion sensor.

Figure 5:
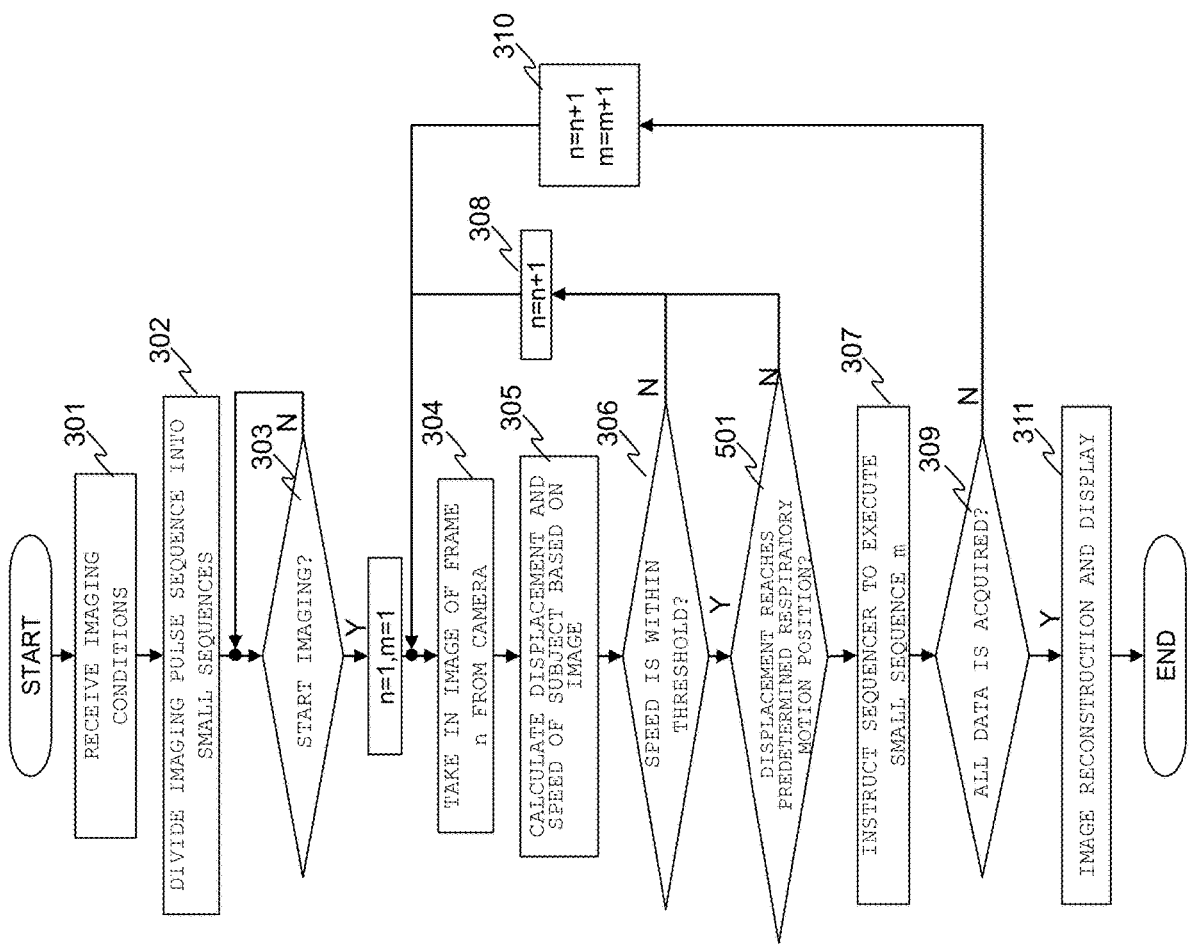
FIG. 5 is a flowchart showing operations of the central processing unit 110 of an MRI apparatus according to a second embodiment.

The MRI apparatus according to the second embodiment will be specifically described with reference to a flow of FIG. 5 and FIG. 6. Since the MRI apparatus according to the second embodiment has the same hardware configuration as that of the first embodiment, a description thereof will be omitted.

Steps 301 to 306

The central processing unit 110 of the MRI apparatus according to the second embodiment performs steps 301 to 305 in the same manner as in the first embodiment to divide an imaging pulse sequence into small sequences corresponding to a frame rate, and to calculate the motion and the displacement of the subject based on images of the camera 200.

The second embodiment is different from the first embodiment in that the central processing unit 110 calculates both the displacement and the motion of the subject 10 in step 305, and determines, in step 306, presence or absence of a sudden motion of the subject 10 based on the motion calculated in step 305. When the motion is within the allowable range, the process proceeds to step 501. When the motion exceeds the allowable range, the process returns to step 304 as in the first embodiment.

Steps 501 and 307

The central processing unit 110 determines whether the displacement of the subject 10 calculated in step 305 reaches a predetermined position in a predetermined respiratory cycle.

Specifically, when a predetermined synchronous position of the respiratory motion is, for example, a predetermined displacement position during inhalation, the central processing unit 110 proceeds to step 307 and instructs the sequencer 120 to execute a small sequence when the motion calculated in step 305 is positive and the displacement reaches the predetermined synchronous position.

Steps 307 to 311

By performing steps 307 to 311 in the same manner as in the first embodiment, the central processing unit 110 sequentially executes the small sequences m (m=1 to 256 or 512) to acquire all the echo signals m (m=1 to 256 or 512). The central processing unit 110 performs image reconstruction using all the obtained echo signals to reconstruct a tomographic image or the like.

Figure 6:
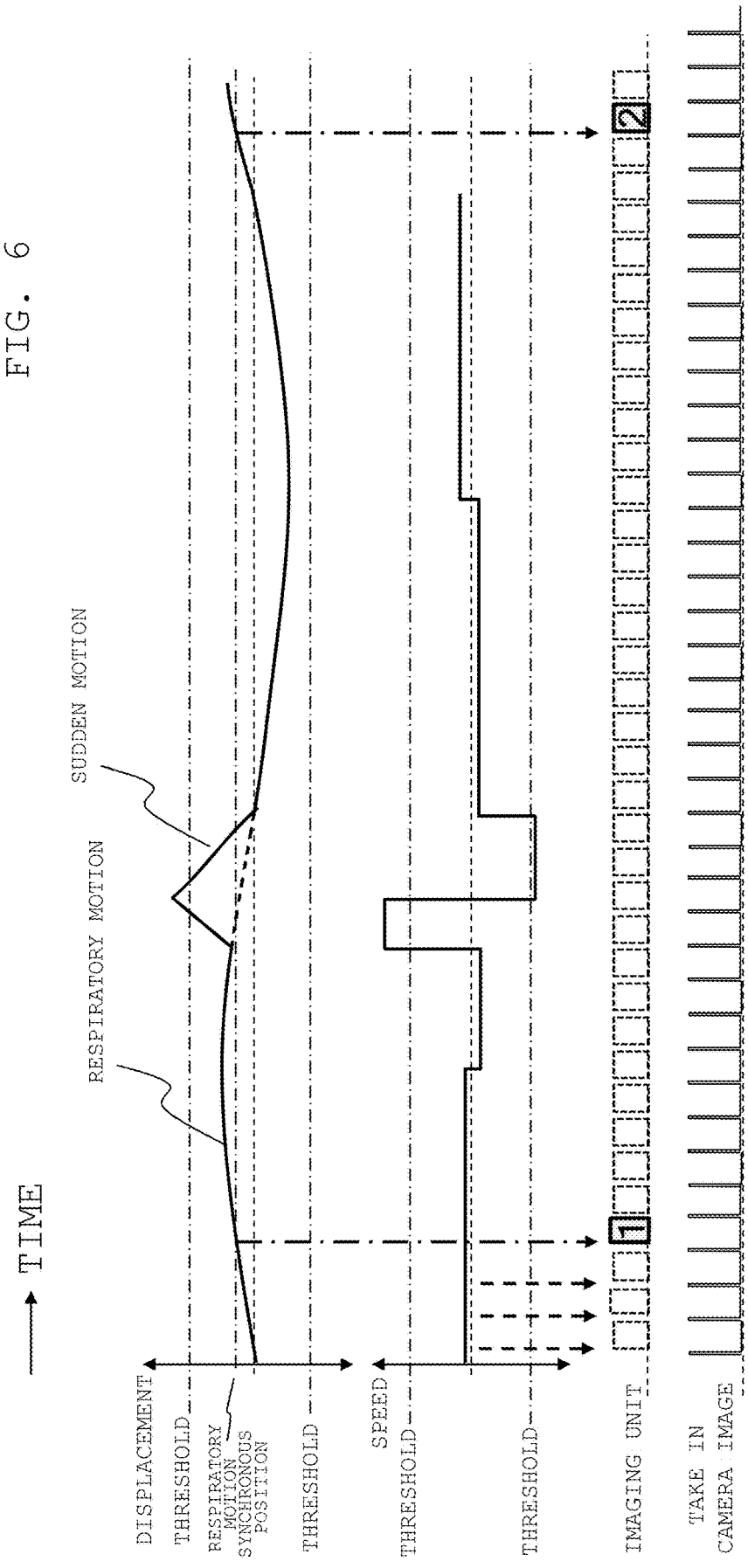
FIG. 6 is a time chart showing a displacement and a motion of a subject, timings for the central processing unit 110 of the MRI apparatus to take in camera images, and imaging periods of the imaging unit 300 according to the second embodiment.

In the second embodiment, as is clear from FIG. 6, only when the motion of the subject 10 is within the allowable range and the displacement caused by the respiratory motion of the subject reaches the predetermined synchronous position, the small sequence is executed immediately thereafter to acquire an echo signal. Therefore, the acquired echo signal is not affected by the sudden motion of the subject 10, and it is possible to generate the tomographic image of the subject 10 in a state in which the displacement caused by the respiratory motion is at the predetermined synchronous position.

In the second embodiment described above, the central processing unit 110 determines whether a sudden motion occurs in the subject based on the motion (speed) of the subject, but may also perform the determination based on the displacement of the subject as described in the first embodiment.

In addition, in the second embodiment, both the determination of the presence or absence of the sudden motion and respiratory motion synchronization are performed, but it is also possible to capture an image by only performing the respiratory motion synchronization, as a matter of course. In this case, it is possible to implement imaging of the respiratory motion synchronization by only performing the steps other than step 306 in FIG. 5.

In the second embodiment described above, it is determined whether the displacement caused by the respiratory motion is at the predetermined synchronous position, but the present embodiment is not limited to the respiratory motion, and can be similarly applied to any cyclic displacement of the subject. For example, imaging can be performed in synchronization with a cyclic displacement of a chest caused by heartbeats or a cyclic displacement of a neck or the like caused by pulsation.

Third Embodiment

An MRI apparatus according to a third embodiment will be described.

Similar to the second embodiment, the third embodiment is an embodiment in which imaging is performed when a displacement of the subject 10 reaches a predetermined respiratory motion position according to a cycle of a respiratory motion. In the second embodiment, one small sequence is imaged in each respiratory cycle, but in the third embodiment, the cycle of the respiratory motion of the subject 10 is detected, and an intermediate sequence in which some small sequences are collected is set in accordance with the cycle of the respiratory motion, or the intermediate sequence is proposed to an operator so that the intermediate sequence can be imaged in each respiratory cycle. Accordingly, NMR data for the intermediate sequence can be acquired in each cycle.

Hereinafter, description will be made with reference to flowcharts of FIG. 7 and FIG. 8. In the flowchart of FIG. 7, the same steps as those in the flowchart of FIG. 5 according to the second embodiment are denoted by the same reference numerals.

Steps 301 and 302

The central processing unit 110 performs steps 301 and 302 to divide an imaging pulse sequence into small sequences corresponding to a frame rate.

Steps 701 and 702

Next, the central processing unit 110 takes in an image of the camera 200 and calculates the displacement of the subject with respect to a reference position based on the image.

Step 703

The central processing unit 110 detects a cyclic motion of the subject 10 based on the calculated displacement, obtains a cycle of the cyclic motion, and determines a length t of time that enables appropriate imaging.

For example, as shown in FIG. 8, a predetermined period of inhalation is set as a period that enables imaging, and a length t thereof is obtained.

Step 704

The central processing unit 110 collects a plurality of small pulse sequences divided in step 302 so as to fall within the length t, and sets an intermediate pulse sequence. Alternatively, the intermediate pulse sequence is proposed to the operator. In addition, the central processing unit 110 may change other imaging parameters or propose the operator for changing the imaging parameters.

Steps 303 to 305, and 501

Thereafter, when the operator instructs to start imaging, the central processing unit 110 takes in a camera image and calculates the displacement of the subject based on the taken in image of a frame n (n=1) as in the first and second embodiments (steps 303 to 305). The central processing unit 110 determines whether the displacement of the subject 10 calculated in step 305 reaches a predetermined position in a predetermined respiratory cycle (step 501).

When the calculated displacement reaches the predetermined position in the predetermined respiratory cycle, the central processing unit 110 proceeds to step 705 and instructs the sequencer 120 to execute the intermediate sequence. Since only a series of intermediate sequences are executed during execution of step 705, processing of steps 304, 305, and 501 may be interrupted. Due to the interruption, it is possible to reduce a load on the central processing unit. Alternatively, steps 304, 305, and 501 may be continuously performed to detect a sudden motion of the subject 10 that occurs during the execution of step 705.

Steps 309 and 311

The central processing unit 110 repeats steps 304, 305, 501, and 705 to sequentially execute the intermediate sequences and acquire all echo signals. The central processing unit 110 performs image reconstruction using all the obtained echo signals to reconstruct a tomographic image or the like.

In this manner, in the MRI apparatus according to the third embodiment, the small sequences are collected in accordance with the respiratory cycle of the subject 10, and the intermediate sequence is set and executed in synchronization with respiration. In the second embodiment, data cannot be acquired unless sequential image processing is performed without interruption. However, in the third embodiment, real-time image processing is required only until a trigger for starting execution of the intermediate sequence is acquired. Therefore, sequential image processing can be omitted while the imaging sequence is executed, and the processing can be performed even when calculation capability of an arithmetic processing device is insufficient.

In the third embodiment, in step 305, not only the displacement but also the motion of the subject 10 may be calculated as well, and when the motion exceeds a threshold, only data in a time period in which the motion exceeds the threshold among the NMR data obtained by the intermediate sequence or the entire data obtained by the intermediate sequence may be discarded, and then the intermediate pulse sequence may be executed again to acquire an NMR signal.

What is claimed is:

1. A magnetic resonance imaging apparatus comprising:
   a static magnetic field generating device configured to apply a static magnetic field to an imaging region;
   an imaging unit including an RF signal irradiation device configured to irradiate a subject arranged in the imaging region with a high-frequency magnetic field pulse, and a gradient magnetic field generating device configured to generate a gradient magnetic field pulse, the imaging unit acquiring a nuclear magnetic resonance signal generated from the subject in response to the high-frequency magnetic field pulse and the gradient magnetic field pulse;
   a processing device coupled to the imaging unit, the processing device controlling the imaging unit to repeatedly execute the application of the high-frequency magnetic field pulse and the gradient magnetic field pulse and the acquisition of the nuclear magnetic resonance signal at predetermined timings in accordance with a predetermined imaging pulse sequence and controlling the imaging unit to acquire a necessary number of nuclear magnetic resonance signals for image reconstruction; and
   a camera configured to continuously and optically image the subject arranged in the imaging region during an operation of the imaging unit, wherein
   the processing device takes in images captured by the camera at a predetermined frame rate,
   the imaging pulse sequence is divided into small sequences at a time width corresponding to the frame rate, and
   the processing device controls the imaging unit to sequentially execute the small sequences at a time interval corresponding to the frame rate by repeating an operation of: before controlling the imaging unit to execute one small sequence, detecting a displacement of the subject with respect to a predetermined reference position or a motion speed of the subject based on an image of the latest frame taken in at the frame rate, and controlling the imaging unit to execute the small sequence when a detection result is within a predetermined allowable range and waiting until an image of a next frame is taken in according to the frame rate without causing the imaging unit to execute the small sequence when the detection result exceeds the allowable range.

2. The magnetic resonance imaging apparatus according to claim 1, wherein the processing device detects at least the displacement based on the image of the latest frame, determines whether the detected displacement reaches a predetermined displacement caused by a predetermined cyclic motion of the subject, and control the imaging unit to execute the small sequence when the detection result is within the predetermined allowable range and the displacement of the subject reaches the predetermined displacement caused by the predetermined cyclic motion.

3. The magnetic resonance imaging apparatus according to claim 1, wherein
   the processing device detects a cyclic displacement of the subject based on images of a plurality of frames, obtains a time width in which a nuclear magnetic resonance signal can be acquired based on a cycle of the detected displacement, and generates an intermediate sequence by collecting a plurality of small sequences so as to fall within the time width, and
   the processing device then takes in the image of the latest frame to detect a displacement, determines whether the cyclic displacement of the subject reaches a predetermined displacement, and controls the imaging unit to execute the intermediate sequence when the cyclic displacement reaches the predetermined displacement.

4. The magnetic resonance imaging apparatus according to claim 1, wherein the processing device receives the frame rate via an operating device.

5. A magnetic resonance imaging apparatus comprising:
   a static magnetic field generating device configured to apply a static magnetic field to an imaging region;
   an imaging unit including an RF signal irradiation device configured to irradiate a subject arranged in the imaging region with a high-frequency magnetic field pulse, and a gradient magnetic field generating device configured to generate a gradient magnetic field pulse, the imaging unit acquiring a nuclear magnetic resonance signal generated from the subject in response to the high-frequency magnetic field pulse and the gradient magnetic field pulse;
   a processing device coupled to the imaging unit, the processing device controlling the imaging unit to repeatedly execute the application of the high-frequency magnetic field pulse and the gradient magnetic field pulse and the acquisition of the nuclear magnetic resonance signal at predetermined timings in accordance with a predetermined imaging pulse sequence and controlling the imaging unit to acquire a necessary number of nuclear magnetic resonance signals for image reconstruction; and
   a camera configured to continuously and optically image the subject arranged in the imaging region during an operation of the imaging unit, wherein
   the processing device takes in images captured by the camera at a predetermined frame rate,
   the imaging pulse sequence is divided into small sequences at a time width corresponding to the frame rate, and
   the processing device controls the imaging unit to sequentially execute the small sequences by repeating an operation of: before controlling the imaging unit to execute one small sequence, detecting a displacement of the subject based on an image of the latest frame taken in at the frame rate, determining whether the detected displacement reaches a predetermined displacement caused by a predetermined cyclic motion of the subject, and controlling the imaging unit to execute the small sequence when the detected displacement reaches the predetermined displacement and waiting until an image of a next frame is taken in according to the frame rate without executing the small sequence when the detected displacement does not reach the predetermined displacement.

6. The magnetic resonance imaging apparatus according to claim 5, wherein the processing device receives the frame rate via an operating device.

7. The magnetic resonance imaging apparatus according to claim 5, wherein the processing device detects at least the displacement based on the image of the latest frame, determines whether the detected displacement reaches a predetermined displacement caused by a predetermined cyclic motion of the subject, and causes the imaging unit to execute the small sequence when the detection result is within the predetermined allowable range and the displacement of the subject reaches the predetermined displacement caused by the predetermined cyclic motion.

8. The magnetic resonance imaging apparatus according to claim 5, wherein
the processing device detects a cyclic displacement of the subject based on images of a plurality of frames, obtains a time width in which a nuclear magnetic resonance signal can be acquired based on a cycle of the detected displacement, and generates an intermediate sequence by collecting a plurality of small sequences so as to fall within the time width, and
the processing device then takes in the image of the latest frame to detect a displacement, determines whether the cyclic displacement of the subject reaches a predetermined displacement, and causes the imaging unit to execute the intermediate sequence when the cyclic displacement reaches the predetermined displacement.

9. A magnetic resonance imaging apparatus comprising:
a static magnetic field generating device configured to apply a static magnetic field to an imaging region;
an imaging unit including an RF signal irradiation device configured to irradiate a subject arranged in the imaging region with a high-frequency magnetic field pulse, and a gradient magnetic field generating device configured to generate a gradient magnetic field pulse, the imaging unit acquiring a nuclear magnetic resonance signal generated from the subject in response to the high-frequency magnetic field pulse and the gradient magnetic field pulse; and
a processing device coupled to the imaging unit, the processing device controlling the imaging unit to repeatedly execute the application of the high-frequency magnetic field pulse and the gradient magnetic field pulse and the acquisition of the nuclear magnetic resonance signal at predetermined timings in accordance with a predetermined imaging pulse sequence and controlling the imaging unit to acquire a necessary number of nuclear magnetic resonance signals for image reconstruction, wherein
the processing device takes in images from a camera connected to the processing device at a predetermined frame rate,
the imaging pulse sequence is divided into small sequences at a time width corresponding to the frame rate, and
the processing device controls the imaging unit to sequentially execute the small sequences at a time interval corresponding to the frame rate by repeating an operation of: before controlling the imaging unit to execute one small sequence, detecting a displacement of the subject with respect to a predetermined reference position or a motion speed of the subject based on an image of a latest frame taken in at the frame rate, and controlling the imaging unit to execute the small sequence when a detection result is within a predetermined allowable range and waiting until an image of a next frame is taken in according to the frame rate without causing the imaging unit to execute the small sequence when the detection result exceeds the allowable range.

10. The magnetic resonance imaging apparatus according to claim 9, wherein the processing device receives the frame rate via an operating device.

11. The magnetic resonance imaging apparatus according to claim 9, wherein the processing device detects at least the displacement based on the image of the latest frame, determines whether the detected displacement reaches a predetermined displacement caused by a predetermined cyclic motion of the subject, and causes the imaging unit to execute the small sequence when the detection result is within the predetermined allowable range and the displacement of the subject reaches the predetermined displacement caused by the predetermined cyclic motion.

12. The magnetic resonance imaging apparatus according to claim 9, wherein
the processing device detects a cyclic displacement of the subject based on images of a plurality of frames, obtains a time width in which a nuclear magnetic resonance signal can be acquired based on a cycle of the detected displacement, and generates an intermediate sequence by collecting a plurality of small sequences so as to fall within the time width, and
the processing device then takes in the image of the latest frame to detect a displacement, determines whether the cyclic displacement of the subject reaches a predetermined displacement, and causes the imaging unit to execute the intermediate sequence when the cyclic displacement reaches the predetermined displacement.

13. A method for controlling a magnetic resonance imaging apparatus which applies a high-frequency magnetic field pulse and a gradient magnetic field pulse to a subject arranged in an imaging region at a timing according to a predetermined imaging pulse sequence and acquires a nuclear magnetic resonance signal generated from the subject, the method comprising:
taking in images from a camera connected to the magnetic resonance imaging apparatus at a predetermined frame rate; and
causing the magnetic resonance imaging apparatus to sequentially execute small sequences, obtained by dividing the imaging pulse sequence so as to have a time width corresponding to the frame rate, at a time interval corresponding to the frame rate by repeating an operation of:
detecting a displacement of the subject with respect to a predetermined reference position or a motion speed of the subject based on an image of the latest frame taken in at the frame rate, and
causing the magnetic resonance imaging apparatus to execute the small sequences when a detection result is within a predetermined allowable range and waiting until an image of a next frame is taken in according to the frame rate without executing the small sequences when the detection result exceeds the allowable range.

14. A non-transitory storage medium storing a control program of a magnetic resonance imaging apparatus which applies a high-frequency magnetic field pulse and a gradient magnetic field pulse to a subject placed in an imaging region at a timing according to a predetermined imaging pulse sequence and acquires a nuclear magnetic resonance signal generated from the subject, the control program causing a computer to execute a process comprising: a step of taking in an image of the subject from a camera connected to the magnetic resonance imaging apparatus at a predetermined frame rate; a step of detecting a displacement of the subject with respect to a predetermined reference position or a motion speed of the subject based on an image of the latest frame, which is taken in at the frame rate; and a step of causing the magnetic resonance imaging apparatus to sequentially execute small sequences obtained by dividing the imaging pulse sequence so as to have a time width corresponding to the frame rate when a detection result is within a predetermined allowable range, and waiting until an image of a next frame is taken in according to the frame rate without executing the small sequences when the detection result exceeds the allowable range.

* * * * *